(12) United States Patent
Sterin

(10) Patent No.: US 7,943,747 B2
(45) Date of Patent: *May 17, 2011

(54) ORGANOSILICON COMPOUNDS AND PROCESS FOR THE PREPARATION THEREOF

(75) Inventor: Sebastien Sterin, Saint Cyr Au Mont d'Or (FR)

(73) Assignee: Rhodia Chimie, Aubervilliers (FR)

( * ) Notice: Subject to any disclaimer, the term of this patent is extended or adjusted under 35 U.S.C. 154(b) by 155 days.

This patent is subject to a terminal disclaimer.

(21) Appl. No.: 11/921,012

(22) PCT Filed: May 17, 2006

(86) PCT No.: PCT/FR2006/001109
§ 371 (c)(1),
(2), (4) Date: Feb. 25, 2009

(87) PCT Pub. No.: WO2006/125889
PCT Pub. Date: Nov. 30, 2006

(65) Prior Publication Data
US 2009/0216001 A1 Aug. 27, 2009

(30) Foreign Application Priority Data

May 26, 2005 (FR) ..................... 05 05284

(51) Int. Cl.
*C07F 7/18* (2006.01)
(52) U.S. Cl. ..................................... 534/586
(58) Field of Classification Search .......... None
See application file for complete search history.

(56) References Cited

U.S. PATENT DOCUMENTS

| 4,118,367 A | | 10/1978 | Dawes et al. | |
|---|---|---|---|---|
| 5,362,794 A | * | 11/1994 | Inui et al. | 524/496 |
| 2009/0215999 A1 | * | 8/2009 | Sterin | 534/578 |
| 2009/0216000 A1 | * | 8/2009 | Sterin | 534/586 |

OTHER PUBLICATIONS

Mitchell, H. et al, "Animation of Arenes with Electron-Deficient Azodicarboxylates," J. Org. Chem., 1994, pp. 682-687, vol. 59.
Dawes, K et al., Chemical modification of natural rubber—a new silane coupling agent, Plastics and Rubber: Materials and Applications, Feb. 1978, pp. 23-26, XP0009060017, London, England.
Dawes, K et al., Chemical modification of natural rubber—a new silane coupling agent, Rubbercon '77, 1977, pp. 18.1-18.11.

* cited by examiner

*Primary Examiner* — Fiona T Powers
(74) *Attorney, Agent, or Firm* — Buchanan Ingersoll & Rooney, P.C.

(57) ABSTRACT

Functionalized organosilicon compounds comprising at least one activated azo group of formula (I): $[(G^0)_3SiO_{1/2}]_m$ $[(G^0)_2SiO_{2/2}]_n$ $[G^0SiO_{3/2}]_o$ $[SiO_{4/2}]_p$ $[(G^2)_a(G^1)_{a'}(Z\text{-CO-HN=NH-CO-A})SiO_{(3-a-a')/2}]$, for example a mixture of silane species of formula $(i_a)$: $(C_2H_5O)_3Si-(CH_2)_3-NH-CO-N=N-COOC_2H_5$; with siloxane species of formulae: $(2i.1_a)$: $[(CH_3)_3SiO_{1/2}]$ $[(C_2H_5O)_2$ $\{(CH_2)_3-NH-CO-N=N-COOC_2H_5\}$ $SiO_{2/2}]$ and $(2i.2_a)$: $[(CH_3)_3SiO_{1/2}]_2$ $[(C_2H_5O)$ $\{(CH_2)_3-NH-CO-N=N-COOC_2H_5\}$ $SiO_{2/2}]$, are prepared from at least one hydrazino precursor (II) (—HN—NH—) of compound (I), by oxidizing the precursor (II) into an azo group for the compound (I) utilizing at least one oxidizing agent (Ox) and at least one vase (B) and also a supplementary reagent selected from among silanes of formula (III): (G DEG)4-p1Si $(G^{2'})$p1 [for example, $(CH_3)_3(C_2H_5O)Si$].

10 Claims, No Drawings

ORGANOSILICON COMPOUNDS AND PROCESS FOR THE PREPARATION THEREOF

CROSS-REFERENCE TO PRIORITY/PCT APPLICATIONS

This application claims priority under 35 U.S.C. §119 of FR 05/05284, filed May 26, 2005, and is a continuation of PCT/FR 2006/001109, filed May 17, 2006 and designating the United States (published in the French language on Nov. 30, 2006 as WO 2006/125889 A3; the title and abstract were also published in English), each hereby expressly incorporated by reference in its entirety and each assigned to the assignee hereof.

The field of the invention is the synthesis of organosilicon compounds (e.g. azo-alkoxysilanes).

The invention relates more particularly to organosilicon compounds comprising at least one activated azo group. Said activation can result, for example, from the presence of carbonyl groups near the nitrogens. The organosilicon moiety of these compounds can comprise for example hydrolyzable or condensable groups of type ≡SiOR or ≡SiOH.

Such organosilicon compounds with available activated azo group(s) (for example those with the group —CO—N=N—CO—) are very useful, notably in the synthesis of organic active molecules (for example nitrogen-containing heterocycles) for use in the areas of agrochemistry and pharmacy, for example as dienophiles in a hetero-Diels-Alder reaction.

However, few of these compounds are available, in particular because they are difficult to prepare. It would therefore be desirable to be able to extend the range of organosilicon compounds that are available.

In the sparse prior art, we find patent application FR-A-2340323, which discloses organosilicon compounds of formula (I*):

Y—X—CO—N=N—CO—X$^1$-Z* in which X and X$^1$, which may be identical or different, each represent an imino group, an oxygen atom or a substituted or unsubstituted methylene group; Y is a substituted or unsubstituted alkyl, aryl or aralkyl group, or is identical to Z*; Z* is an alkyl, aryl or aralkyl group with, as substituent, at least one silane group of formula Si(OR)$_3$ or OSi(OR)$_3$ in which R is a linear or branched alkyl group, preferably with 1 to 6 carbon atoms.

Organosilicon compounds of formula (II*) and (III*):

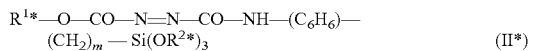

R$^{1*}$—O—CO—N=N—CO—NH—(C$_6$H$_6$)—(CH$_2$)$_m$—Si(OR$^{2*}$)$_3$     (II*)

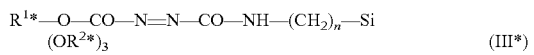

R$^{1*}$—O—CO—N=N—CO—NH—(CH$_2$)$_n$—Si(OR$^{2*}$)$_3$     (III*)

in which R$^{1*}$ and R$^{2*}$, which may be identical or different, each represent a linear or branched alkyl group preferably containing between 1 and 6 carbon atoms, m is equal to 0, 1, 2 or 3 and n is equal to 1, 2 or 3, are mentioned.

A compound of formula Ethyl-O—CO—N=N—CO—NH—(CH$_2$)$_3$—Si(OEthyl)$_3$, according to formula (III*), is disclosed in example 3.

The key stage in the synthesis of organosilicon compounds of this type with an activated azo group comprises the oxidation of a group of the hydrazo (NH—NH) type to a corresponding azo (N=N) group.

According to FR-A-2340323, this transformation is carried out using an oxidizing system comprising an oxidizing agent formed by a halogenated derivative and a base of the pyridine type. This type of base has the drawback that it leads to products containing pyridine residues, the presence of which is disadvantageous for the quality of the final product, notably on the one hand in terms of industrial hygiene and ecotoxicity, and on the other hand in terms of performance in applications.

Moreover, the organosilicon compounds according to application FR-A-2340323 have the drawback that they contain three hydrolyzable functions Si—OR$^{2*}$ per mole of silicon and may release appreciable amounts of alcohol, during storage in humid conditions. This formation of alcohol is all the more troublesome because in most cases the alcohols produced are volatile organic compounds (VOC) that are hazardous, in particular on account of their toxicity and their flammability.

In this context, one of the main aims of the present invention is to provide novel organosilicon compounds [preferably with activated azo group(s)], which offer better performance than their known homologs, in particular with respect to the presence of undesirable impurities.

Another essential aim of the present invention is to provide novel organosilicon compounds that are easier to prepare than previously.

Another essential aim of the present invention is to provide novel organosilicon compounds that are more economical.

Another essential aim of the present invention is to provide novel organosilicon compounds that are more stable and notably more stable when heated.

Another essential aim of the present invention is to provide novel organosilicon compounds that offer good performance in applications.

Another essential aim of the present invention is to provide novel organosilicon compounds that do not release VOC or release smaller amounts of VOC during storage in a humid atmosphere and/or during application.

Another essential aim of the present invention is to provide novel organosilicon compounds that can be stored in a humid atmosphere.

Another essential aim of the present invention is to provide novel organosilicon compounds, in the preparation of which it is possible to control species that are likely to generate VOC, notably during storage in a humid atmosphere.

Another essential aim of the present invention is to provide an improved method of preparation of organosilicon compounds, said method being of the type involving the oxidation of the hydrazo groups of a precursor to azo groups, and said method offers better performance in terms of productivity/yield, is more economical, is easier to implement and leads to organosilicon compounds that are free or almost free of undesirable impurities.

Another essential aim of the present invention is to provide an improved method of preparation of organosilicon compounds having good performance in applications.

Another essential aim of the present invention is to provide an improved method of preparation of organosilicon compounds that do not release VOC or release smaller amounts of VOC, during storage in a humid atmosphere and/or during application.

Another essential aim of the present invention is to provide an improved method of preparation of organosilicon compounds that makes it possible to control the production of species that are likely to generate VOC, notably during storage in a humid atmosphere.

These aims, among others, are achieved by the present invention, which relates, according to the first of its objects, to functionalized organosilicon compounds comprising one or more species, which may be identical to or different from one another, of general formula (I) specified below:

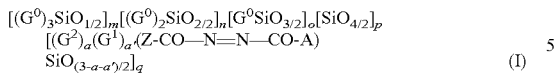

(I)

in which:
- m, n, o, p each represent an integer or fraction greater than or equal to 0;
- q represents an integer or fraction greater than or equal to 1;
- a represents an integer selected from 0, 1, 2 and 3;
- a' represents an integer selected from 0, 1 and 2;
- the sum a+a' is in the range from 0 to 3 with conditions according to which:
  - (C1)—when a=0, then:
    - either at least one of m, n, o, p is a number different from 0 (zero) and q is greater than or equal to 1;
    - or q is greater than 1 and each of m, n, o, p has any value;
    - and at least one of the symbols $G^0$ corresponds to the definition given hereunder for $G^2$;
  - (C2)—when a+a'=3, then m=n=o=p=0 (zero);
  - (C3)—and when the organosilicon compounds are constituted exclusively of compounds of formula (I) in which a=3, q=1, m=n=o=p=0, then the organosilicon compounds of formula (I*), (II*) or (III*) as defined above are excluded,
- the symbols $G^0$, which may be identical or different, each represent one of the groups corresponding to $G^2$ or $G^1$;
- the symbols $G^2$, which may be identical or different, each represent: a hydroxyl group, a hydrolyzable monovalent group or two $G^2$ form together, and with the silicon to which they are attached, a ring having 3 to 5 hydrocarbon ring members and which can contain at least one heteroatom, and at least one of these ring members can also be a ring member of at least one other hydrocarbon or aromatic ring;
- the symbols $G^1$, which may be identical or different, each represent: a saturated or unsaturated aliphatic hydrocarbon group; a saturated or unsaturated and/or aromatic, monocyclic or polycyclic, carbocyclic group; or a group representing a saturated or unsaturated, aliphatic hydrocarbon moiety and a carbocyclic moiety as defined above;
- the symbol Z represents a divalent radical selected from: a saturated or unsaturated aliphatic hydrocarbon group; a saturated, unsaturated and/or aromatic, monocyclic or polycyclic, carbocyclic group; and a group having a saturated or unsaturated, aliphatic hydrocarbon moiety and a carbocyclic moiety as defined above; said divalent radical being optionally substituted or interrupted by an oxygen atom and/or a sulfur atom and/or a nitrogen atom, said nitrogen atom bearing 1 monovalent group selected from: a hydrogen atom; an aliphatic, saturated or unsaturated hydrocarbon atom; a saturated or unsaturated and/or aromatic, monocyclic or polycyclic, carbocyclic group; and a group having a saturated or unsaturated, aliphatic hydrocarbon moiety and a carbocyclic moiety as defined above;
- the symbol A represents:
  - a saturated or unsaturated aliphatic hydrocarbon group; a saturated or unsaturated and/or aromatic, monocyclic or polycyclic, carbocyclic group; or a group representing a saturated or unsaturated, aliphatic hydrocarbon moiety and a carbocyclic moiety as defined above;
  - a group —X-$G^3$ where: X represents —O—, —S— or —N$G^4$- with $G^4$ taking any one of the meanings given previously for $G^1$; $G^3$, identical to or different from $G^4$, represents any one of the groups defined for $G^1$; and the substituents $G^3$ and $G^4$ of the group —N$G^4G^3$ can, in addition, form together, and with the nitrogen atom to which they are attached, a single ring having from 5 to 7 ring members, with the ring containing 3 to 6 carbon atoms, 1 or 2 nitrogen atom(s) and optionally 1 or 2 unsaturated double bond(s);
  - or, when q=1, a group [-Z-SiO$_{(3-a-a')/2}$(G$^2$)$_a$(G$^1$)$_{a'}$][(G$^0$)$_3$SiO$_{1/2}$]$_m$[(G$^0$)$_2$SiO$_{2/2}$]$_n$[G$^0$SiO$_{3/2}$]$_o$[SiO$_{4/2}$]$_p$ in which the symbols Z, $G^1$, $G^2$, a, a', m, n, o, and p have the definitions stated previously.

In the aforementioned formula (I), it has to be understood that the group (Z-CO—N=N—CO-A) is joined to the Si atom of the SiO$_{(3-a-a')/2}$ unit via the divalent radical -Z-.

DEFINITIONS

In the foregoing, aliphatic hydrocarbon group means, in the sense of the invention, a linear or branched group, preferably having from 1 to 25 carbon atoms, and optionally substituted.

Advantageously, said aliphatic hydrocarbon group has from 1 to 18 carbon atoms, better still from 1 to 8 carbon atoms and even better still from 1 to 6 carbon atoms.

We may mention, as examples of a saturated aliphatic hydrocarbon group, the alkyl groups, such as the methyl, ethyl, propyl, isopropyl, n-butyl, isobutyl, t-butyl, pentyl, isopentyl, neopentyl, 2-methylbutyl, 1-ethylpropyl, hexyl, isohexyl, neohexyl, 1-methylpentyl, 3-methylpentyl, 1,1-dimethylbutyl, 1,3-dimethylbutyl, 2-ethylbutyl, 1-methyl-1-ethylpropyl, heptyl, 1-methylhexyl, 1-propylbutyl, 4,4-dimethylpentyl, octyl, 1-methylheptyl, 2-ethylhexyl, 5,5-dimethylhexyl, nonyl, decyl, 1-methymonyl, 3,7-dimethyloctyl and 7,7-dimethyloctyl, and hexadecyl radicals.

The unsaturated aliphatic hydrocarbon groups contain one or more unsaturations, preferably one, two or three unsaturations of the ethylenic type (double bond) and/or acetylenic type (triple bond).

Examples are the alkenyl or alkynyl groups derived from the alkyl groups defined above by elimination of two or more hydrogen atoms. Preferably, the unsaturated aliphatic hydrocarbon groups comprise a single unsaturation.

Within the scope of the invention, carbocyclic group means a monocyclic or polycyclic radical, optionally substituted, preferably of $C_3$-$C_{50}$. Advantageously, it is a $C_3$-$C_{18}$ radical, preferably mono-, bi- or tricyclic. When the carbocyclic group comprises more than one cyclic nucleus (as in the case of polycyclic carbocycles), the cyclic nuclei are condensed two by two. Two condensed nuclei can be orthocondensed or pericondensed.

The carbocyclic group can comprise, unless stated otherwise, a saturated moiety and/or an aromatic moiety and/or an unsaturated moiety.

Examples of saturated carbocyclic groups are the cycloalkyl groups. Preferably, the cycloalkyl groups are of $C_3$-$C_{18}$, and better still of $C_5$-$C_{10}$. We may notably mention the cyclopentyl, cyclohexyl, cycloheptyl, cyclooctyl, adamantyl or norbornyl radicals.

The unsaturated carbocycle or any unsaturated moiety of the carbocyclic type has one or more ethylenic unsaturations, preferably one, two or three. It has advantageously from 6 to 50 carbon atoms, and better still from 6 to 20, for example from 6 to 18. Examples of unsaturated carbocycles are the $C_6$-$C_{10}$ cycloalkenyl groups.

Examples of aromatic carbocyclic radicals are the ($C_6$-$C_{18}$) aryl groups, and better still ($C_6$-$C_{12}$) aryl and notably phenyl, naphthyl, anthryl and phenanthryl.

A group having both an aliphatic hydrocarbon moiety as defined above and a carbocyclic moiety as defined above is, for example, an aralkyl group such as benzyl, or an alkaryl group such as tolyl.

The substituents of the aliphatic hydrocarbon groups or moieties and of the carbocyclic groups or moieties are, for example, alkoxy groups in which the alkyl moiety is preferably as defined above.

By hydrolyzable monovalent group, as was discussed above in connection with the symbols $G^2$, we mean groups such as, for example: halogen atoms, notably chlorine; the groups —O-$G^7$ and —O—CO-$G_7$ where $G_7$ represents: a saturated or unsaturated, aliphatic hydrocarbon group, or a saturated, unsaturated and/or aromatic, monocyclic or polycyclic, carbocyclic group, or a group having a saturated or unsaturated, aliphatic hydrocarbon moiety and a carbocyclic moiety as defined above, and $G_7$ can optionally be halogenated and/or substituted with one or more alkoxy; the groups —O—N=$CG_8G_9$ in which $G_8$ and $G_9$ assume, independently, any one of the meanings given above for $G_7$, and $G_8$ and $G_9$ can be halogenated and/or optionally substituted with one or more alkoxy; the groups —O—$NG_8G_9$ in which $G_8$ and $G_9$ are as defined above.

Advantageously, said hydrolyzable monovalent group is a radical: $C_1$-$C_8$ alkoxy, linear or branched, optionally halogenated and/or optionally substituted with one or more ($C_1$-$C_8$) alkoxy; $C_2$-$C_9$ acyloxy optionally halogenated or optionally substituted with one or more ($C_1$-$C_8$)alkoxy; $C_5$-$C_{10}$ cycloalkyloxy; or $C_6$-$C_{18}$ aryloxy. As an example, the hydrolyzable group is methoxy, ethoxy, n-propoxy, isopropoxy, n-butoxy, methoxymethoxy, ethoxyethoxy, methoxyethoxy, β-chloropropoxy or β-chloroethoxy or alternatively acetoxy.

As monovalent carbocyclic groups that can be formed together, in formula (I), by two substituents $G^2$ and the silicon atom to which they are attached, we may mention for example the ring systems:

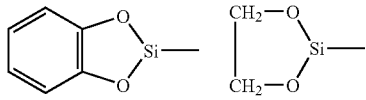

As single rings that can be formed together on the one hand by the substituents $G^3$ and $G^4$ of the nitrogen atom present in symbol A of formula (I) and on the other hand by the substituents $R^2$ and $R^3$ of the nitrogen atom present in symbol J of formula (III), we may mention for example the following rings where the free valence is carried by a nitrogen atom: pyrrole, imidazole, pyrazole, pyrrolidine, Δ2-pyrroline, imidazolidine, Δ2-imidazoline, pyrazolidine, Δ3-pyrazoline, piperidine; preferred examples are: pyrrole, imidazole and pyrazole.

These novel functionalized organosilicon compounds (I) are interesting in several respects: economical, easy to produce, stable (notably stable when heated), they offer good performance in applications, they are only slightly subject, if at all, to reactions of hydrolysis and/or condensation (release of VOC) during storage in a humid atmosphere and during application (controllable sensitivity to hydrolysis/condensation).

In preferred forms F1 of formula (I):
The symbols $G^0$, which may be identical or different, correspond to the same definition as given hereunder for radicals $G^1$ or $G^2$;
The symbols $G_1$, which may be identical or different, each represent: a linear or branched, $C_1$-$C_8$ alkyl radical; a $C_5$-$C_{10}$ cycloalkyl radical or a $C_6$-$C_{18}$ aryl radical;
The symbols $G_2$, which may be identical or different, each represent: a linear or branched, $C_1$-$C_8$ alkoxy radical, optionally substituted with one or more ($C_1$-$C_8$)alkoxy;
Z represents the divalent radical Z'-Z"- where:
Z' represents: a $C_1$-$C_8$ alkylene chain; a $C_5$-$C_{10}$ saturated cycloalkylene group; a $C_6$-$C_{18}$ arylene group; or a divalent group comprising a combination of at least two of these radicals;
Z" represents: —O— or —$NR^4$—, where $R^4$ is: a hydrogen atom; a linear or branched, $C_1$-$C_8$ alkyl radical; a $C_5$-$C_{10}$ cycloalkyl radical; a $C_6$-$C_{18}$ aryl radical; or a ($C_6$-$C_{18}$)aryl-($C_1$-$C_8$)alkyl radical;
A denotes a group —O-$G^3$ or —$NG^4G^3$ where $G^3$ and $G^4$, which may be identical to or different from one another, each represent: a linear or branched, $C_1$-$C_8$ alkyl radical; a $C_5$-$C_{10}$ cycloalkyl radical or a $C_6$-$C_{18}$ aryl radical.

In more preferred forms F2 of formula (I):
The symbols $G^0$, which may be identical or different, correspond to the same definition as that given hereunder for the radicals $G^1$ or $G^2$;
The symbols $G_1$, which may be identical or different, are selected from the group comprising the methyl, ethyl, propyl, isopropyl, cyclohexyl and phenyl radicals;
The symbols $G_2$, which may be identical or different, are selected from the group comprising the methoxy, ethoxy, n-propoxy, isopropoxy, n-butoxy, methoxymethoxy, ethoxyethoxy and methoxyethoxy radicals;
Z represents the divalent radical Z'-Z"- where:
Z' represents: a $C_1$-$C_8$ alkylene chain;
Z" represents: —O— or —$NR^4$—, with $R^4$ being selected from the group comprising: hydrogen, the methyl, ethyl, propyl, isopropyl, n-butyl, isobutyl, t-butyl, pentyl, hexyl, cyclohexyl, and benzyl radicals;
A denotes a group —O-$G^3$ or —$NG^4G^3$ where $G^3$ and $G^4$, which may be identical to or different from one another, are selected from the group comprising the methyl, ethyl, propyl, isopropyl, cyclohexyl and phenyl radicals.

In even more preferred forms F3 of formula (I):
The symbols $G^0$, which may be identical or different, each represent one of the radicals selected hereunder for $G^1$ or $G^2$;
The symbols $G_1$, which may be identical or different, are selected from the group comprising the methyl, ethyl, propyl, isopropyl, cyclohexyl and phenyl radicals;
The symbols $G_2$, which may be identical or different, are selected from the group comprising the methoxy, ethoxy, n-propoxy, isopropoxy and n-butoxy radicals;
Z represents the divalent radical Z'-Z"- where:
Z' is selected from the group comprising the methylene, ethylene and propylene divalent radicals;
Z" represents: —O— or —$NR^4$— with $R^4$ being a hydrogen atom;
A denotes a group —O-$G^3$ where $G^3$ is selected from the group comprising the methyl, ethyl, propyl, isopropyl, cyclohexyl and phenyl radicals.

According to an especially preferred embodiment, the functionalized organosilicon compounds of general formula (I) are selected from the group comprising the following species:

(i) functionalized organosilanes corresponding to formula (I) in which: a+a'=3; m=n=o=p=0 (zero); and q=1;

(2i) functionalized siloxane oligomers corresponding to formula (I) in which: a+a'=1 or 2; m is in the range from 1 to 2; n=p=o=0 (zero); and q=1;

(3i) mixtures of at least one species (i) and/or of at least one species (2i).

Advantageously, species (2i) are divided into subspecies:

(2i.1) functionalized siloxane oligomers corresponding to formula (I) in which: a+a'=2; m=1; n=p=o=0 (zero); and q=1;

(2i.2) functionalized siloxane oligomers corresponding to formula (I) in which: a+a'=1; m=2; n=p=o=0 (zero); and q=1.

According to an interesting variant of the especially preferred embodiment, the functionalized organosilicon compounds of general formula (I) are selected from the group of the following (sub)species:

(i) functionalized organosilanes corresponding to formula (I) in which: a+a'=3; m=n=o=p=0 (zero); and q=1;

(2i.1) functionalized siloxane oligomers corresponding to formula (I) in which: a+a'=2; m=1; n=p=o=0 (zero); and q=1;

(2i.2) functionalized siloxane oligomers corresponding to formula (I) in which: a+a'=1; m=2; n=p=o=0 (zero); and q=1;

(3i) mixtures of at least one species (i) and/or of at least one subspecies (2i.1) and/or of at least one subspecies (2i.2).

Within this variant, functionalized organosilicon compounds of general formula (I) that are particularly preferred are those formed by a mixture (3i) of at least one species (i) and/or of at least one subspecies (2i.1) and/or of at least one subspecies (2i.2).

In practice, it is possible for the organosilicon compounds according to the invention to comprise at least one mixture (3i) including compounds (i) and/or (2i.1) and/or (2i.2) of formula (I) in which:

The symbols $G^0$, which may be identical or different, correspond to the definitions given below for $G^1$, $G^2$;

The symbols $G_1$, which may be identical or different, are selected from the group comprising the methyl, ethyl, propyl, isopropyl, cyclohexyl and phenyl radicals;

The symbols $G_2$, which may be identical or different, are selected from the group comprising the methoxy, ethoxy, n-propoxy, isopropoxy and n-butoxy radicals;

A denotes a group —O-$G^3$ where $G^3$ is selected from the group comprising the methyl, ethyl, propyl, isopropyl, cyclohexyl and phenyl radicals.

Z represents the divalent radical Z'-NR$^4$— where:

Z' is selected from the group comprising the methylene, ethylene and propylene divalent radicals;

R$^4$ is a hydrogen atom.

The present invention also relates to functionalized organosilicon compounds comprising at least one mixture (3i) in which the organosilicon compounds constituted exclusively of compounds of formula (I) in which: a=3, q=1, m=n=o=p=0 (zero), can include organosilicon compounds of formula (I*), (II*) or (III*) as defined above.

Preferably, mixture (3i) has the following composition (in mol. %):

30 to 95, preferably 60 to 90 of silanes (i);

and 5 to 70, preferably 5 to 40 of siloxanes (2i.1 and/or 2i.2).

As examples of functional organosilicon compounds (i), (2i.1) and (2i.2) with azo groups, we may mention the products with the following formulas:

species (i) where a=3, a'=0, m=n=o=p=0 (zero) and q=1:

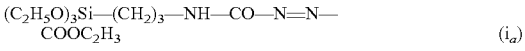(i$_a$)

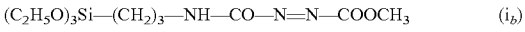(i$_b$)

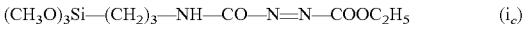(i$_c$)

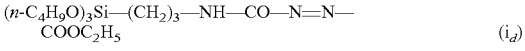(i$_d$)

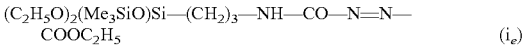(i$_e$)

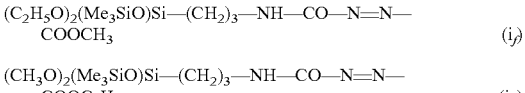(i$_f$)

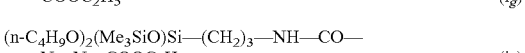(i$_g$)

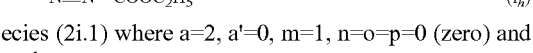(i$_h$)

species (2i.1) where a=2, a'=0, m=1, n=o=p=0 (zero) and q=1:

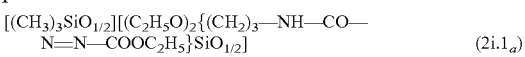(2i.1$_a$)

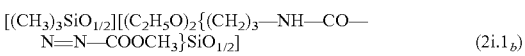(2i.1$_b$)

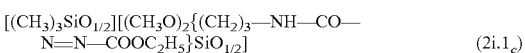(2i.1$_c$)

species (2i.2) where a=1, a'=0, m=2, n=o=p=0 (zero) and q=1:

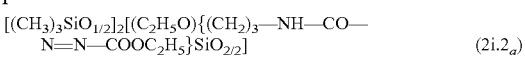(2i.2$_a$)

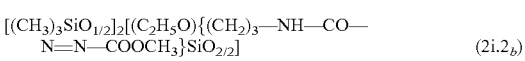(2i.2$_b$)

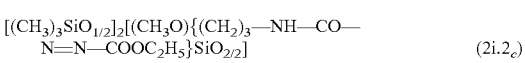(2i.2$_c$)

According to an advantageous feature of the invention, the organosilicon compounds (I) under consideration only contain traces of alcohol (notably of VOC), or are even alcohol-free.

A second object of the invention comprises a method of preparation of organosilicon compounds (notably but non-limitatively those constituting the first object of the invention) comprising one or more compounds, which may be identical to or different from one another, of formula (I) specified hereunder:

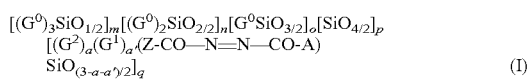(I)

in which:

m, n, 0, p each represent an integer or fraction greater than or equal to 0;

q represents an integer or fraction greater than or equal to 1;

a represents an integer selected from 0, 1, 2 and 3;

a' represents an integer selected from 0, 1 and 2;

the sum a+a' is in the range from 0 to 3 with conditions according to which:

(C1)—when a=0, then:

either at least one of m, n, o, p is a number different from 0 (zero) and q is greater than or equal to 1;

or q is greater than 1 and each of m, n, o, p has any value;

and at least one of the symbols $G^0$ corresponds to the definition given hereunder for $G^2$;

(C2)—when a+a' 3, then m=n=o=p=0 (zero);

the symbols $G^0$, which may be identical or different, each represent one of the groups corresponding to $G^2$ or $G^1$;

the symbols $G^2$, which may be identical or different, each represent: a hydroxyl group, a hydrolyzable monovalent group or two $G^2$ form together, and with the silicon to which they are attached, a ring having 3 to 5 hydrocarbon ring members and which can contain at least one heteroatom, and at least one of these ring members can also be a ring member of at least one other hydrocarbon or aromatic ring;

the symbols $G^1$, which may be identical or different, each represent: a saturated or unsaturated aliphatic hydrocarbon group; a saturated or unsaturated and/or aromatic, monocyclic or polycyclic, carbocyclic group; or a group representing a saturated or unsaturated, aliphatic hydrocarbon moiety and a carbocyclic moiety as defined above;

the symbol Z represents a divalent radical selected from: a saturated or unsaturated aliphatic hydrocarbon group; a saturated, unsaturated and/or aromatic, monocyclic or polycyclic, carbocyclic group; and a group having a saturated or unsaturated, aliphatic hydrocarbon moiety and a carbocyclic moiety as defined above; said divalent radical being optionally substituted or interrupted by an oxygen atom and/or a sulfur atom and/or a nitrogen atom, said nitrogen atom bearing 1 monovalent group selected from: a hydrogen atom; an aliphatic, saturated or unsaturated hydrocarbon atom; a saturated or unsaturated and/or aromatic, monocyclic or polycyclic, carbocyclic group; and a group having a saturated or unsaturated, aliphatic hydrocarbon moiety and a carbocyclic moiety as defined above;

the symbol A represents:

a saturated or unsaturated aliphatic hydrocarbon group; a saturated or unsaturated and/or aromatic, monocyclic or polycyclic, carbocyclic group; or a group representing a saturated or unsaturated, aliphatic hydrocarbon moiety and a carbocyclic moiety as defined above;

a group —X-$G^3$ where: X represents —O—, —S— or —N$G^4$- with $G^4$ taking any one of the meanings given previously for $G^1$; $G^3$, identical to or different from $G^4$ represents any one of the groups defined for $G^1$; and the substituents $G^3$ and $G^4$ of the group —N$G^4G^3$ can, in addition, form together, and with the nitrogen atom to which they are attached, a single ring having from 5 to 7 ring members, with the ring containing 3 to 6 carbon atoms, 1 or 2 nitrogen atom(s) and optionally 1 or 2 unsaturated double bond(s);

or, when q=1, a group [-Z-SiO$_{(3-a-a')/2}$($G^2$)$_a$($G^1$)$_{a'}$] [($G^0$)$_3$SiO$_{1/2}$]$_m$[($G^0$)$_2$SiO$_{2/2}$]$_n$[$G^0$SiO$_{3/2}$]$_o$[SiO$_{4/2}$]$_p$ in which the symbols Z, $G^1$, $G^2$, a, a', m, n, o, and p have the definitions stated previously;

this method being of the type of those comprising:

employing at least one precursor (II) of at least one organosilicon compound (I), said precursor corresponding to the following formula (II):

[($G^0$)$_3$SiO$_{1/2}$]$_m$[($G^0$)$_2$SiO$_{2/2}$]$_n$[$G^0$SiO$_{3/2}$]$_o$[SiO$_{4/2}$]$_p$
[($G^2$)$_a$($G^1$)$_{a'}$(Z-CO—HN—NH—CO-A)
SiO$_{(3-a-a')/2}$]$_q$       (II)

in which the symbols $G^0$, $G^1$, $G^2$, Z, A, m, n, o, p, a, a' and q are as defined above under formula (I), oxidizing the hydrazino group of precursor (II) to an azo group belonging to the organosilicon compound (I), by means of an oxidizing system comprising at least one oxidizing agent (Ox) and at least one base (B), and this method being characterized in that notably it envisages:

selecting base B from the inorganic bases, preferably from the inorganic bases of formula (B): $M_2CO_3$ in which M is a metal—preferably an alkali metal;

selecting Ox from the oxidizing agents that are able to oxidize a hydrazine group to an azo group, preferably from the halogens, cyanides and chlorine-containing compounds and mixtures thereof, and even more preferably from the group comprising: bromine, tert-butyl hypochlorite, trichloroisocyanuric acid, chlorine and mixtures thereof;

and employing an additional reagent selected from the silanes (used alone or mixed together) of formula (III):

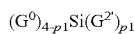

in which:

the symbols $G^0$, which may be identical or different, each represent: a saturated or unsaturated aliphatic hydrocarbon group; a saturated or unsaturated and/or aromatic, monocyclic or polycyclic, carbocyclic group; or a group representing a saturated or unsaturated, aliphatic hydrocarbon moiety and a carbocyclic moiety as defined above; or a polysiloxane residue;

the symbols $G^{2'}$, which may be identical or different, represent a hydrolyzable monovalent group corresponding to the same definition as that given above for the symbols $G^2$ described in connection with formula (I);

p1 represents an integer selected from 1 and 2, preferably 1.

The inventors were able to combine a selection of bases B, a selection of oxidizing agents Ox and the use of one or more alkoxysilanes, making it unnecessary to use pyridine as base B. This greatly simplifies the preparation of the organosilicon compounds with azo groups of formula (I), as it is not necessary to carry out a post-treatment for removing pyridine residues.

This result is achieved without affecting the performance of the method (yield/productivity), nor the quality of the product, whilst allowing the method to become more economical.

Moreover, this method provides access to novel products comprising several organosilicon compounds with azo groups of formula (I), excluding the organosilicon compounds of formula (I*), (II*) or (III*) as defined above, when the compounds in question are composed exclusively of compounds of formula (I) in which: a=3, q=1, m=n=o=p=0 (zero).

The organosilicon compounds with azo groups of formula (I) obtained are notably those selected from the group comprising the following species:

(i) functionalized organosilanes corresponding to formula (I) in which: a+a'=3; m=n=o=p=0 (zero); and q=1;

(2i) functionalized siloxane oligomers corresponding to formula (I) in which: a+a'=1 or 2; m is in the range from 1 to 2; n=p=o=0 (zero); and q=1;

(3i) mixtures of at least one species (i) and/or of at least one species (2i).

The functionalized siloxane oligomers (2i) and the mixtures (3i) of at least one species (i) and of at least one species (2i) are novel as such without excluding the organosilicon compounds of formula (I*), (II*) or (III*) as defined above, when the compounds in question are composed exclusively of compounds of formula (I) in which: a=3, q=1, m=n=o=p=0 (zero).

In general, the definition of organosilicon compounds with azo groups of formula (I) obtained by the method according to the invention returns to the definitions given above in the description of organosilicon compounds (I) used as such.

Preferably, the method is applied in an anhydrous medium, preferably in organic solution.

The solvents selected are, for example, those belonging to the following classes of solvents: chlorine-containing solvents such as dichloromethane and chloroform, aromatic solvents such as toluene, xylene or monochlorobenzene, ethers such as tetrahydrofuran, reagents (III) and mixtures thereof.

It was found to be quite desirable, according to the invention, to select B from bases of the carbonate type, in particular of sodium. One of the advantages of bases B of this type is that they make it unnecessary to use pyridine.

According to a preferred embodiment, this method is employed at room temperature and/or at atmospheric pressure.

According to a remarkable feature, the method according to the invention essentially comprises the following stages:
mix the precursor (II), the base (B), the additional reagent (III), an organic solvent and an oxidizing agent (Ox), the latter preferably being added progressively to the reaction mixture over a few minutes to a few hours;
leave to react, preferably with stirring;
filter the reaction mixture, removing any excess of base (B) by formation of a salt MOx;
and, optionally, concentrate.

According to a particularly advantageous embodiment of the method according to the invention, Ox is used in stoichiometric amounts relative to precursor (II). For example, Ox can be used at a rate of 1M stoichiometric.

According to another particularly advantageous embodiment of the method according to the invention, B is used in stoichiometric amounts relative to the amount of acid released by the reaction.

The amount of additional reagent (III) used is not critical, but it is preferable, according to the invention, for said amount, relative to precursor (II), to be at least 0.1M, preferably from at least 1M up to 100M or more, and even more preferably between 1 and 10M.

Advantageously, the organosilicon compounds with azo group obtained by the method according to the invention only contain traces of alcohol, or none at all. "Alcohol" notably denotes, in the sense of the present description, VOC.

The method according to the invention for the preparation of the organosilicon compounds with azo group (I) can be included in a method of synthesis comprising at least the following stages:
(i): react a precursor silane of formula (IV):

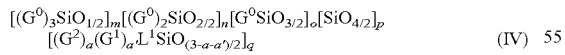

with a precursor hydrazo derivative of formula (V):

$L^2$-NH—NH—CO-A    (V)

formulas in which the symbols $G^0$, $G^1$, $G^2$, m, n, o, p, q, a, a' and A are as defined previously, and $L^1$ and $L^2$ represent groups whose structure and functionality are such that these groups are able to react with one another to give rise to the central linkage -Z-CO— so as to lead to the precursor of formula (II):

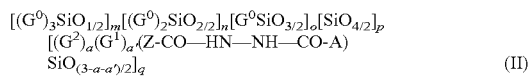

(ii): submit the precursor of formula (II) to a reaction of oxidation of the hydrazo group —HN—NH— to an azo group —N=N—.

The oxidation in stage (ii) corresponds to the method of preparation according to the present invention.

For the preparation, for example, of organosilicon compounds with an azo group (I), in the structure of which the symbol Z then represents the divalent radical —$(CH_2)_3$—NH—, the following synthesis scheme can be applied:
(i): react a precursor silane of formula (IV):

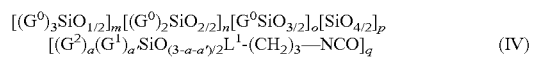

with a precursor hydrazo derivative of formula (V):

$H_2N$—NH—CO-A    (V)

to obtain the hydrazo compound of formula (II):

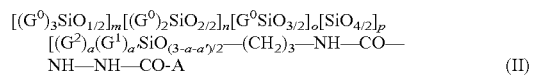

(ii): submit the compound of formula (II) to a reaction of oxidation of the hydrazo group —HN—NH— to an azo group —N=N—.

To summarize, stage (i) of obtaining precursor (II) and stage (ii) of oxidation of (II) to (I) comply with the following general methodology:

STAGE (i):

Use of a precursor hydrazo derivative of formula (V) and solvent, at the ambient temperature in the reactor, under an inert atmosphere.

Stirring at several hundred rev/min and heating at T=40-100° C.

Addition of the precursor silane of formula (IV) in several tens of minutes.

Reaction for several hours with stirring at T=40-100° C. before returning to room temperature.

Rest for a few hours at room temperature.

Recovery of the solid (for example) precursor of formula (II), filtration, washing, drying.

STAGE (ii):

Application of precursor (II), Ox (for example Ox2) and solvent at the ambient temperature in the reactor, under an inert atmosphere.

Addition of Ox (for example Ox1) to the reactor in several tens of minutes, at a temperature below 30° C., preferably 25° C.

Stirring at room temperature for several hours.

Concentration.

Recovery of the organosilicon compounds with activated azo functional group(s) (I).

Washing, filtration.

Concentration.

For more details about the novel organosilicon compounds according to the invention as well as the practical methodology employed, reference may be made to the examples given below. The following examples illustrate the scope of the method presented above.

EXAMPLES

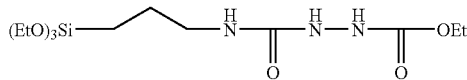

Et=Ethyl monovalent radical

Example 1

Put 10 g (28.4 mmol, 1 eq) of compound 1, 7.53 g (71 mmol, 2.5 eq) of dry $Na_2CO_3$, 10.06 g (85.2 mmol, 3 eq) of trimethylethoxysilane and 50 mL of dichloromethane in a 250-mL reactor. Add, dropwise, a solution of 4.55 g of bromine (28.4 mmol, 1 eq) in 15 mL of dichloromethane, in 1 hour.

Stir the reaction mixture for an additional 30 minutes after the end of addition of the bromine. Then filter the reaction mixture and concentrate under vacuum. 8.28 g of a bright-orange thin liquid is obtained.

Analysis by $^1$H-NMR shows that compound 1 has been consumed completely, that the azo group has been formed selectively and that there is limited loss of the SiOEt group. The molar composition of the final product is shown in Table 1.

Example 2

Put 10 g (28.4 mmol, 1 eq) of compound 1, 7.53 g (71 mmol, 2.5 eq) of dry $Na_2CO_3$ and 50 mL of a 50/50 (vol/vol) mixture of trimethylethoxysilane and dichloromethane in a 250-mL reactor. Add, dropwise, a solution of 4.55 g of bromine (28.4 mmol, 1 eq) in 15 mL of dichloromethane, in 1 hour. Stir the reaction mixture for an additional 30 minutes after the end of addition of the bromine.

Then filter the reaction mixture and concentrate under vacuum. 9.77 g of a bright-orange thin liquid is obtained.

Analysis by $^1$H-NMR shows that compound 1 has been consumed completely, that the azo group has been formed selectively and that there is limited loss of the SiOEt. The molar composition of the final product is shown in Table 1.

Example 3

Put 10 g (28.4 mmol, 1 eq) of compound 1, 3.31 g (31.2 mmol, 1.1 eq) of dry $Na_2CO_3$ and 50 mL of a 50/50 (vol/vol) mixture of trimethylethoxysilane and dichloromethane in a 250-mL reactor. Add, dropwise, a solution of 4.55 g of bromine (28.4 mmol, 1 eq) in 15 mL of dichloromethane, in 1 hour. Stir the reaction mixture for an additional 30 minutes after the end of addition of the bromine.

Then filter the reaction mixture and concentrate under vacuum. 9.78 g of a bright-orange thin liquid is obtained.

Analysis by $^1$H-NMR shows that compound 1 has been consumed completely, that the azo group has been formed selectively and that there is limited loss of the SiOEt group. The molar composition of the final product is shown in Table 1.

The final product obtained in Examples 1 to 3 is a mixture:
of the silane species of formula:

$(C_2H_5O)_3Si$—$(CH_2)_3$—NH—CO—N=N—COOC$_2$H$_3$     (i$_a$)

with the siloxane species of formulae:

$[(CH_3)_3SiO_{1/2}][(C_2H_5O)_2\{(CH_2)_3$—NH—CO—N=N—COOC$_2$H$_5\}SiO_{1/2}]$     (2i.1$_a$) and $[(CH_3)_3SiO_{1/2}]_2[(C_2H_5O)\{(CH_2)_3$—NH—CO—N=N—COOC$_2$H$_5\}SiO_{2/2}]$     (2i.2$_a$)

the molar proportions of which are shown in Table 1.

TABLE 1

|  | Species (i$_a$): | Species (2i-1$_a$) | Species (2i.2$_a$) | Loss of SiOEt functions |
|---|---|---|---|---|
| Example 1 | 62% | 33% | 5% | 14.3% |
| Example 2 | 81% | 12% | 7% | 8.7% |
| Example 3 | 63% | 26% | 11% | 16% |

The invention claimed is:
1. A process for the preparation of an organosilicon compound of the following formula (I):

$$[(G^0)_3SiO_{1/2}]_m[(G^0)_2SiO_{2/2}]_n[G^0SiO_{3/2}]_o[SiO_{4/2}]_p$$
$$[(G^2)_a(G^1)_{a'}(Z\text{-CO}-N=N-\text{CO-A})$$
$$SiO_{(3-a-a'/2)}]_q \qquad (I)$$

in which:
m, n, o, p each represent an integer or fraction greater than or equal to 0;
q represents an integer or fraction greater than or equal to 1;
a represents an integer selected from 0, 1, 2 and 3;
a' represents an integer selected from 0, 1 and 2;
the sum a+a' ranges from 0 to 3, with the proviso that:
(C1) when a=0, then:
either at least one of m, n, o, p is a number different from 0 (zero) and q is greater than or equal to 1;
or q is greater than 1 and each of m, n, o, p has any value; and
at least one of the symbols $G^0$ is as defined hereunder for $G^2$;
(C2) when a+a'=3, then m=n=o=p=0 (zero);
the symbols $G^0$, which may be identical or different, each represent one of the following groups $G^2$ or $G^1$;
the symbols $G^2$, which may be identical or different, each represent a hydroxyl group, a hydrolyzable monovalent group or two groups $G^2$ may together form, with the silicon from which they depend, a ring having 3 to 5 hydrocarbon ring members and which can contain at least one heteroatom, and at least one of these ring members can also be a ring member of at least one other hydrocarbon or aromatic ring;
the symbols $G^1$, which may be identical or different, each represent a saturated or unsaturated aliphatic hydrocarbon group; a saturated, unsaturated or aromatic monocyclic carbocyclic group; a polycyclic carbocyclic group comprising at least one of a saturated ring, an unsaturated ring and an aromatic ring; or a group representing a saturated or unsaturated, aliphatic hydrocarbon moiety and a carbocyclic moiety as defined above;
the symbol Z represents a divalent radical selected from a saturated or unsaturated aliphatic hydrocarbon group; a saturated, unsaturated or aromatic monocyclic carbocyclic group; a polycyclic carbocyclic group comprising at least one of a saturated ring, an unsaturated ring and an aromatic ring; and a group having a saturated or unsaturated, aliphatic hydrocarbon moiety and a carbocyclic moiety as defined above; said divalent radical being optionally substituted or interrupted by an oxygen atom and/or a sulfur atom and/or a nitrogen atom, said nitrogen atom, if present, bearing 1 monovalent group selected from a hydrogen atom; an aliphatic, saturated or unsaturated hydrocarbon atom; a saturated or unsaturated and/or aromatic, monocyclic or polycyclic, carbocyclic group; and a group having a saturated or unsaturated, aliphatic hydrocarbon moiety and a carbocyclic moiety as defined above;

the symbol A represents:

a saturated or unsaturated aliphatic hydrocarbon group; a saturated, unsaturated or aromatic monocyclic carbocyclic group; a polycyclic carbocyclic group comprising at least one of a saturated ring, an unsaturated ring and an aromatic ring, or a group representing a saturated or unsaturated, aliphatic hydrocarbon moiety and a carbocyclic moiety as defined above;

a group —X-$G^3$ wherein X represents —O—, —S— or —N$G^4$- wherein $G^4$ is as defined above for $G^1$; $G^3$, identical to or different from $G^4$, represents any one of the groups defined for $G^1$; and the substituents $G^3$ and $G^4$ of the group —N$G^4G^3$ may together form, with the nitrogen atom from which they depend, a single ring having from 5 to 7 ring members, with the ring containing 3 to 6 carbon atoms, 1 or 2 nitrogen atom(s) and optionally 1 or 2 unsaturated double bond(s);

or, when q=1, a group [-Z-SiO$_{(3-a-a'/2)}$($G^2$)$_a$($G^1$)$_{a'}$][($G^0$)$_3$SiO$_{1/2}$]$_m$ [($G^0$)$_2$SiO$_{2/2}$]$_n$ [$G^0$SiO$_{3/2}$]$_o$ [SiO$_{4/2}$]$_p$ in which the symbols Z, $G^1$, $G^2$, a, a', m, n, o, and p are as defined above;

said process comprising:

providing at least one precursor (II) of at least one organosilicon compound (I), said precursor having the following formula (II):

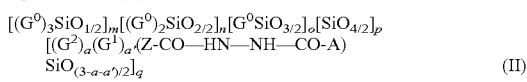

(II)

in which the symbols $G^0$, $G^1$, $G^2$, Z, A, m, n, o, p, a, a' and q are as defined above under formula (I), oxidizing the hydrazino group of precursor (II) to an azo group belonging to the organosilicon compound (I), by means of an oxidizing system which comprises at least one oxidizing agent (Ox) and at least one base (B), said base B comprising an inorganic base of formula (B): M$_2$CO$_3$ in which M is a metal, selecting Ox from among the oxidizing agents that oxidize a hydrazine group to an azo group;

and further employing an additional reagent selected from among the silanes, whether alone or mixed, of formula (III):

in which:

the symbols $G^0$, which may be identical or different, each represent a saturated or unsaturated aliphatic hydrocarbon group; a saturated, unsaturated or aromatic monocyclic carbocyclic group; a polycyclic carbocyclic group comprising at least one of a saturated ring, an unsaturated ring and an aromatic ring;

or a group representing a saturated or unsaturated, aliphatic hydrocarbon moiety and a carbocyclic moiety as defined above; or a polysiloxane residue;

the symbols $G^{2'}$, which may be identical or different, represent a hydrolyzable monovalent group corresponding to the same definition as that given above for the symbols $G^2$ in formula (I); and p1 represents an integer selected from 1 and 2.

2. The process as defined by claim 1, conducted in an anhydrous medium.

3. The process as defined by claim 1, conducted at room temperature and/or at atmospheric pressure.

4. The process as defined by claim 1, wherein:

the precursor (II), the base (B), the additional reagent (III), an organic solvent and an oxidizing agent (Ox) are mixed together, the latter optionally being added progressively to the reaction mixture over a few minutes to a few hours;

permitting the reaction mixture to react, optionally with stirring;

filtering the reaction mixture, removing any excess of base (B) by formation of a salt MOx;

and, optionally, concentrating the reaction mixture.

5. The process as defined by claim 4, wherein Ox is (are) employed in stoichiometric amounts relative to precursor (II).

6. The process as defined by claim 4, wherein B is employed in stoichiometric amounts relative to the amount of acid released by the reaction.

7. The process as defined by claim 4, wherein the amount of additional reagent (III) employed, relative to precursor (II), is at least 0.1 M.

8. The process as defined by claim 4, wherein the organosilicon compound(s) obtained contain only traces of alcohol, or are even free of alcohol.

9. The process as defined by claim 1, wherein prior to oxidation of the hydrazo group —HN—NH— of the precursor of formula (II), to an azo group —N=N—, same comprises at least the following stage of synthesis of precursor (II):

reacting a precursor silane of formula (IV):

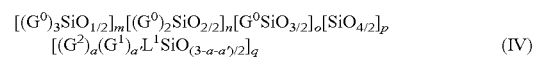

(IV)

with a precursor hydrazo derivative of formula (V):

$L^2$-NH—NH—CO-A   (V)

in which the symbols $G^0$, $G^1$, $G^2$, m, n, o, p, q, a, a' and A are as defined and $L^1$ and $L^2$ represent groups whose structure and functionality are such that these groups are able to react with one another to provide the central linkage -Z-CO— and form the precursor of formula (II):

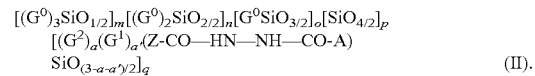

(II).

10. The process as defined by claim 9, comprising the following steps:

STAGE (i):

providing a precursor hydrazo derivative of formula (V) and solvent, at ambient temperature in a reactor, under an inert atmosphere, stirring at several hundred rev/min and heating at T=40°-100° C.

addition of the precursor silane of formula (IV) over several tens of minutes, reacting the mixture for several hours with stirring at T=40°-100° C. and then returning same to room temperature, maintaining the reaction mixture at rest for a few hours at room temperature and recovering the solid precursor of formula (II), followed by filtration, washing, drying.

STAGE (ii): forming a reaction mixture by introducing precursor (II), Ox and solvent at ambient temperature in the reactor, under an inert atmosphere,
  adding Ox to the reactor over several tens of minutes, at a temperature below 30° C., and
  stirring at room temperature for several hours,
  concentrating said reaction mixture,
  recovering a compound of formula (I),
  washing, filtering, and
  concentrating the reaction mixture remaining after the recovery of the compound of formula (I).

* * * * *